United States Patent [19]
Moot

[11] 4,091,589
[45] May 30, 1978

[54] ELEMENT FOR BUILDING CONTRACTION OR EXPANSION JOINTS AND COMPOSITE UNIT OBTAINED WITH THIS ELEMENT

[75] Inventor: Willem H. Moot, Rhode-St-Genese, Belgium

[73] Assignee: S.I.P., s.p.r.l., Rhode-St-Genese, Belgium

[21] Appl. No.: 755,059

[22] Filed: Dec. 28, 1976

[30] Foreign Application Priority Data

Jan. 8, 1976 Belgium ................................. 254748
Nov. 23, 1976 Belgium ................................. 255481

[51] Int. Cl.² ............................................. E04B 1/68
[52] U.S. Cl. ..................................................... 52/573
[58] Field of Search ........................ 404/47, 51, 53, 56, 404/57, 58; 52/573, 417

[56] References Cited

U.S. PATENT DOCUMENTS

| 2,072,381 | 3/1937 | Post ......................................... 404/53 |
| 2,296,756 | 9/1942 | Yeoman ................................. 404/47 |
| 2,319,049 | 5/1943 | Fischer ................................... 404/53 |
| 3,822,428 | 7/1974 | Stog ........................................ 52/573 |

FOREIGN PATENT DOCUMENTS 2,304,840 10/1973 Germany ............................... 404/53

Primary Examiner—John E. Murtagh
Attorney, Agent, or Firm—Bacon & Thomas

[57] ABSTRACT

The invention pertains to a single element for building contraction or expansion joints of the type made up of a base, of which one half of the upper surface is provided with anchoring elements or connecting reinforcements, characterized by the fact that it consists of a thin quadrangular base plate out of some material which can be welded and/or cast and which has a great tensile strength.

5 Claims, 10 Drawing Figures

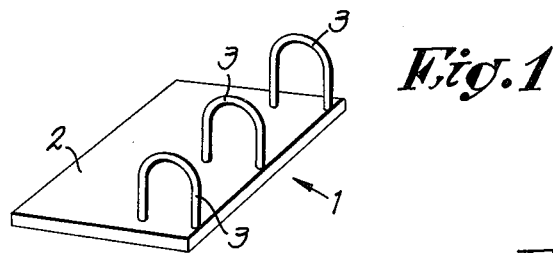
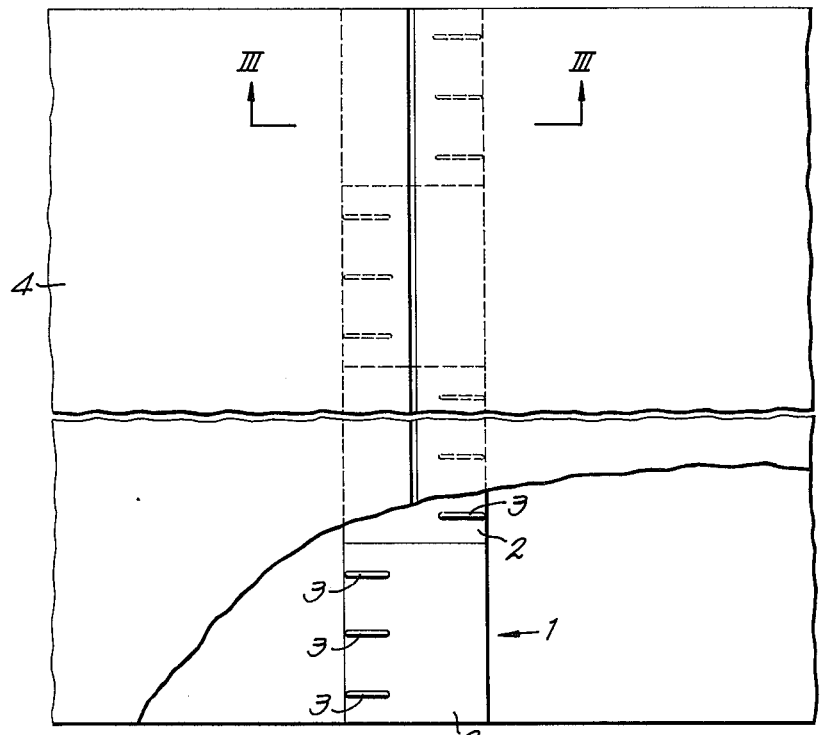
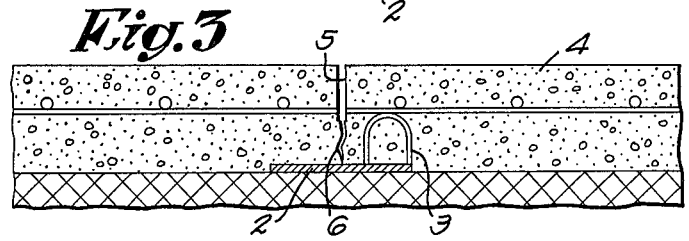
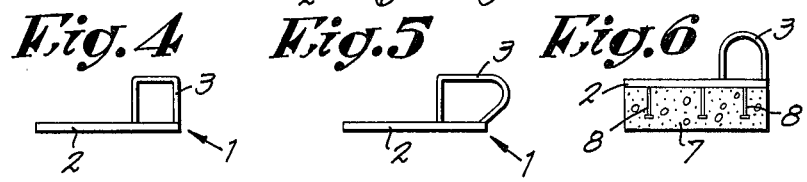

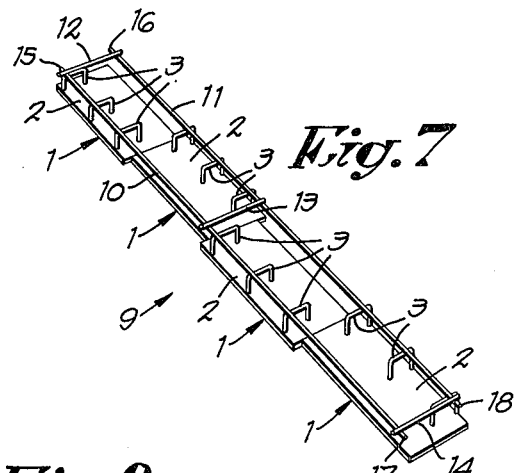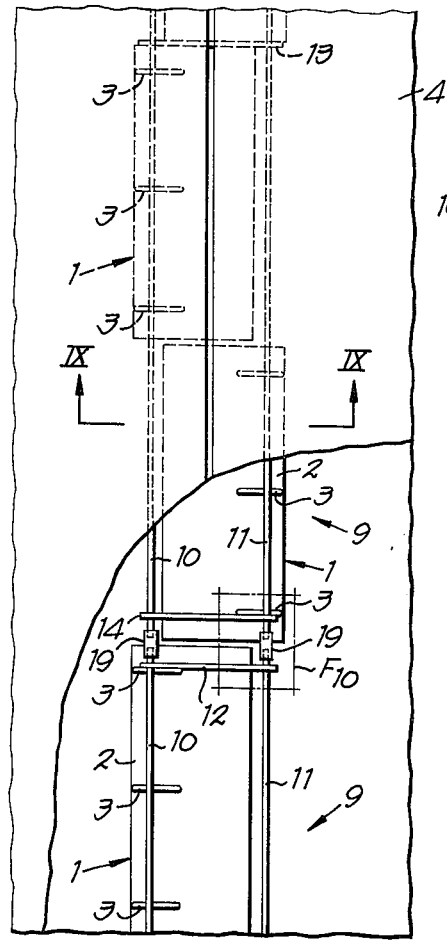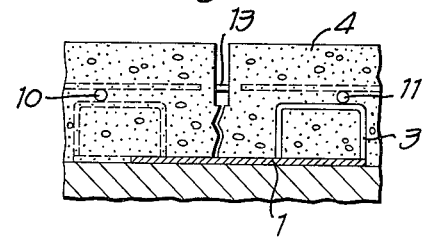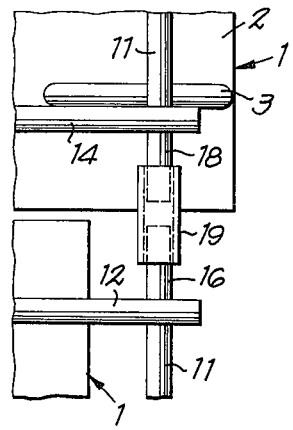

ELEMENT FOR BUILDING CONTRACTION OR EXPANSION JOINTS AND COMPOSITE UNIT OBTAINED WITH THIS ELEMENT

The present invention pertains, on the one hand, to elements for building contraction or expansion joints, and, on the other hand, to composite units obtained by means of such elements, particularly elements for building contraction or expansion joints without differential setting, for any civil engineering works such as roads, airfield runways, circulating areas, parking and storage areas, cold storage depots, floating slabs or coverings, channels, tunnels, buildings and suchlike.

A first characteristic of the invention consists in the fact that the base of the element is made of a material such as steel or other, thus avoiding, with respect to the known concrete elements, amongst others the pouring and the drying of these elements.

A further characteristic of the invention is that the elements are built in such a manner that their presence causes no appreciable weakening of the slabs in which they are incorporated, which permits the sawing out of the roots of cracks as quickly as would be required by the known distribution elements.

Another characteristic of the invention consists in that the elements concerned may be incorporated in slabs or coverings which are markedly thinner than those which have to be used with the known concrete elements.

Yet another characteristic of the invention consists in the fact that the distribution elements can be used in coverings which are traditionally much thinner than the concrete coverings, such as for instance hydrocarbonous coverings or suchlike.

Still a further characteristic consists in the possibility of incorporating the elements for building contraction or expansion joints within the thickness of the covering, even in the case of considerable floor loads, whereas in such cases the known distribution elements have to be located in trenches which are subjacent to the slab.

Another characteristic is that of considerably reducing the weight with respect to the known concrete elements, and consequently greatly to reducing the transport costs and the installation costs of the elements according to the invention.

Another characteristic of the invention consists in that the attachment of the connection reinforcements can be carried out by welding, considering both the base and the reinforcements are made of steel. In one particular form of embodiment, the base and the connection reinforcement may be made integral by casting.

Another characteristic of the invention consists in the joining together, by a rigid link, at least two of aforesaid load transfer elements, so as to avoid the relative movement of these single light elements.

Another characteristic of the invention is that the composite units, being heavier than the single elements, have greater stability when being installed.

A further characteristic consists in the fact that the composite units greatly facilitate the handling and the speed of installation with respect to the single elements.

Yet a further characteristic of the invention is that the load transfer elements of the composite units are arranged in such a manner that they increase the length of the area where the sawing has to be carried out; it is thus absolutely assuring that the sawing is done correctly.

Another characteristic of the invention consists in the linking together of the composite units amongst themselves by means of a device which permits as easy integration and alignment of these elements.

Another characteristic of the invention consists in the fact that the devices which are parallel to the center line of the joints also serve as supports for the reinforcements of the slab.

Another characteristic of the invention consists in the use of load transfer elements and their linking devices which are parallel to the center line of the joint, the height of which is such that the assembly is always located below the reinforcement network of the slab, and consequently permits the use of all the above-mentioned types of reinforcements, irrespective of the size of their meshes.

The single elements according to the invention mainly consist of a thin quadrangular base of some material which can be welded and/or cast and having considerable tensile strength.

The composite units according to the invention are made up mainly of at least two single elements, one half of the upper surface of which is provided with anchoring elements or connection reinforcements, these plates being located and respectively attached one behind the other, whereby the connecting reinforcements are fitted in straddled arrangement.

In order to emphasize the characteristics of the invention more clearly, preferred forms of embodiment are described hereinafter, without the slightest intent of limitation, with reference to the appended drawings, in which:

FIG. 1 shows a perspective view of a single element according to the invention;

FIG. 2 shows a schematic top view of a circulating area at the location of a contraction or expansion joint according to the invention;

FIG. 3 is a section according to line III—III in FIG. 2;

FIGS. 4 and 5 show side views of two alternative forms of embodiment for the element of FIG. 1;

FIG. 6 shows a side view of an element according to the invention, in a mixed steel and concrete form of embodiment;

FIG. 7 shows a perspective view of a composite unit according to the invention;

FIG. 8 shows a schematic top view of a circulating area at the location of a contraction or expansion joint built with composite units according to the invention;

FIG. 9 shows, to a larger scale, a section according to line IX—IX in FIG. 8; and FIG. 10 is an enlargement of the part marked $F_{10}$ in FIG. 8.

In FIG. 1, an element 1 according to the invention is shown, this element being made up of a base 2 of quadrangular shape, and anchoring means or connection reinforcements 3 in the shape of stirrups. These connection reinforcements are located on the upper surface of base 2, and this in such a manner as to occupy only one half of said upper surface of the base.

In a well known manner, these elements are lined up beneath the slab 4, preferably with the insertion between elements 1 of some compressible material, not shown in the drawings, the stirrups 3 being located in straddled array — see FIG. 2 — so that the elements 1 are alternately integral with the one or the other of slabs 4, after the slab has been provided with a slot 5 as a start for a crack 6.

It is quite obvious that such elements 1 may be manufactured out of any sort of material, although they should preferably be made out of steel.

In a first form of embodiment, the stirrups 3 are attached to the base 2 by welding.

In another form of embodiment, the elements may be obtained as integral parts by casting.

In both cases, these elements shall preferably be made out of a stainless steel, or of some steel which is conditioned with an anticorrosion paint and is sufficiently resistant to abrasion.

In FIGS. 4 and 5, further examples are shown of elements 1, of which the shape of the stirrups 3 differs.

Finally, an application is shown in FIG. 6, in which the element 1 is solidly attached to a base 7, for instance of concrete, this attachment being obtained by means of anchoring elements 8.

In FIG. 7, a composit unit 9 according to the invention is shown. This composite unit is made up of several single load transfer elements 1, as previously described.

In the example of FIG. 7, four elements 1 are located the one behind the other so as to form an alignment. The stirrups 3 being placed in straddled arrangement, and the elements 1 being solidly linked together at the top of their connecting reinforcements 3 by a linking element which is made up of side members, respectively 10 and 11, and of cross members, in the present case 12-13 and 14. The cross members 12 and 14 shall preferably be attached at a certain distance from the end of side members 10 and 11, so that these may form guiding rods, respectively 15-16-17 and 18.

These composite units are fitted in alignment under the slab 4, composite units 9 being preferably attached to each other by means of bushings 19, into which are entered the coaxial guiding rods 15-16-17 and 18 of the adjoining composite units.

The resistance of cross members 12-13-14 must be such, that the latter may distort or fail in the course of contraction or expansion movements of the slab, without disturbing the functioning of the joint.

It is quite evident that the linking element 10 to 14 may be made out of any appropriate material. These elements shall however preferably be manufactured out of steel.

In a preferred embodiment, the side members 10 and 11 as well as the cross members 12-13-14 shall be attached to each other and to the connecting reinforcements 3 of elements 1 by means of welding.

It is perfectly clear that the invention is by no means limited to the forms of embodiment described above and illustrated in the appended drawings. All possible alternative forms may be suggested without going beyond the scope of the invention.

What I claim is:

1. Composite construction unit for building contraction or expansion joints and intended for being incorporated in concrete slabs, said composite construction unit including a plurality of aligned construction elements each having a substantially quadrangular base plate made of a material having a relatively high tensile strength, e.g. steel, and a plurality of connecting reinforcements integrally secured to one half of the upper surface of said base plate, said connecting reinforcements being intended to be incorporated in said concrete slabs, said aligned construction elements being positioned in such a way that their connecting reinforcements are staggered and said aligned construction elements being secured to each other by a plurality of linking elements, said connecting reinforcements being arranged in rows and one said linking element being provided per row, each said linking element including at least one linking member, the linking elements forming a linking member being linked together by bushings.

2. Composite construction unit for building contraction or expansion joints and intended for being incorporated in concrete slabs, said composite construction unit inculding a plurality of aligned construction elements each having a substantially quadrangular base plate made of a material having a relatively high tensile strength, e.g. steel, and a plurality of connecting reinforcements integrally secured to one half of the upper surface of said base plate, said connecting reinforcements being intended to be incorporated in said concrete slabs, said aligned construction elements being positioned in such a way that their connecting reinforcements are staggered and said aligned construction elements being secured to each other by a plurality of linking elements, said linking elements being secured to the upper part of said connecting reinforcements e.g. by welding.

3. Composite construction unit according to claim 1, including four of said construction elements.

4. Composite construction unit for building contraction or expansion joints and intended for being incorporated in concrete slabs, said composite construction unit including a plurality of aligned construction elements each having a substantially quadrangular base plate made of a material having a relatively high tensile strength, e.g. steel, and a plurality of connecting reinforcements integrally secured to one half of the upper surface of said base plate, said connecting reinforcements being intended to be incorporated in said concrete slabs, said aligned construction elements being positioned in such a way that their connecting reinforcements are staggered and said aligned construction elements being secured to each other by a plurality of linking elements, said linking elements being connected to each other by at least one cross-member by connecting means.

5. Composite construction unit according to claim 4, wherein the resistance of said cross-members and of said connecting means are such that said cross-members and said connecting means may be ruptured or distorted in the course of contraction and expansion movements of said slabs without disturbing the functioning of the joint.

* * * * *